(12) United States Patent
Legerton

(10) Patent No.: US 9,283,401 B2
(45) Date of Patent: *Mar. 15, 2016

(54) EYE-WEAR BORNE ELECTROMAGNETIC RADIATION REFRACTIVE THERAPY

(71) Applicant: Myolite, Inc., Jupiter, FL (US)

(72) Inventor: Jerome A. Legerton, Jupiter, FL (US)

(73) Assignee: MYOLITE, INC., Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/503,127

(22) Filed: Sep. 30, 2014

(65) Prior Publication Data

US 2015/0018599 A1    Jan. 15, 2015

Related U.S. Application Data

(63) Continuation of application No. 13/859,584, filed on Apr. 9, 2013, now Pat. No. 8,876,284.

(60) Provisional application No. 61/635,712, filed on Apr. 19, 2012.

(51) Int. Cl.
| | |
|---|---|
| *G02C 7/04* | (2006.01) |
| *A61N 2/00* | (2006.01) |
| *G02C 11/04* | (2006.01) |
| *A61B 3/00* | (2006.01) |
| *G02C 11/00* | (2006.01) |
| *G02C 7/08* | (2006.01) |

(52) U.S. Cl.
CPC .............. *A61N 2/004* (2013.01); *A61B 3/0008* (2013.01); *G02C 7/04* (2013.01); *G02C 7/049* (2013.01); *G02C 7/086* (2013.01); *G02C 11/00* (2013.01); *G02C 11/04* (2013.01); *G02C 2202/24* (2013.01)

(58) Field of Classification Search
CPC ....... A61B 3/0008; A61F 9/00; A61F 9/0079; G02C 7/04; G02C 7/049; G02C 7/14; G02C 11/00; G02C 11/04; G02C 11/10
USPC ..................... 351/158, 221, 159.02
See application file for complete search history.

(56) References Cited

U.S. PATENT DOCUMENTS

| 5,682,210 A | 10/1997 | Weirich |
| 7,018,040 B2 | 3/2006 | Blum et al. |

(Continued)

FOREIGN PATENT DOCUMENTS

DE    102010016629 A1 *  1/2006  ........... A61B 3/0008

OTHER PUBLICATIONS

Patent Cooperation Treaty, PCT/ISA/210, International Search Report for PCT/US2013/035851, Jul. 24, 2013, pp. 1-2.

*Primary Examiner* — Huy K Mai
(74) *Attorney, Agent, or Firm* — Sheppard Mullin Richter & Hampton LLP

(57) ABSTRACT

An eye-wear borne electromagnetic radiation refractive therapy system can comprise an electromagnetic radiation source comprising a ring of LEDs that directs one of its on axis or off axis electromagnetic radiation to a desired peripheral retina area of a wearer's eye; a power source for powering the LEDs, an antenna for receiving signals and a processor for controlling the LEDs; wherein the electromagnetic radiation source includes spectral characteristics similar to outdoor light.

19 Claims, 6 Drawing Sheets

(56) References Cited

U.S. PATENT DOCUMENTS

| | | |
|---|---|---|
| 8,092,013 B2 | 1/2012 | Pugh et al. |
| 8,876,284 B2* | 11/2014 | Legerton ................... 351/158 |
| 2009/0033866 A1 | 2/2009 | Blum et al. |
| 2010/0073635 A1 | 3/2010 | Legerton et al. |
| 2010/0103369 A1 | 4/2010 | Pugh et al. |
| 2010/0110372 A1 | 5/2010 | Pugh et al. |
| 2011/0313058 A1 | 12/2011 | Neitz et al. |
| 2012/0199995 A1* | 8/2012 | Pugh et al. ................... 264/1.36 |

* cited by examiner

EYE-WEAR BORNE ELECTROMAGNETIC RADIATION REFRACTIVE THERAPY

CROSS-REFERENCE TO RELATED APPLICATIONS

This application is a continuation of U.S. patent application Ser. No. 13/859,584 filed Apr. 9, 2013, which claims the benefit of U.S. Provisional Patent Application No. 61/635,712 filed Apr. 19, 2012, the contents of which are incorporated herein by reference in their entireties.

FIELD OF THE INVENTION

The present invention relates generally to refractive therapy, and more particularly, to devices and methods for eye-wear borne electromagnetic radiation refractive therapy.

BACKGROUND OF THE INVENTION

Refractive correction is achieved through use of spectacle lenses, contact lenses, corneal refractive surgery and intraocular lens implantation. Contact lenses have evolved from non-gas-permeable rigid lenses which contact the sclera and vault the cornea to corneal contact lenses made of gas permeable products, and then to corneal-scleral contact lenses made of hydrogel materials. Hybrid lenses were created to provide the improved optics of rigid lenses with the comfort of soft lenses. Hybrid lenses were configured to have a central rigid zone joined at a radial junction to a peripheral hydrogel zone. Composite lenses have a full soft layer and those having only an annulus of soft posterior to the rigid layer have been anticipated.

Hybrid lenses of this configuration enjoy commercial success with limitations due to the separation of the two materials at their radial junction, lens flexure and tear stagnation due to a circumferential sealing of the lens against the underlying eye. Advanced manufacturing processes and ultra high gas permeable materials have stimulated a resurgence of fully rigid scleral lens designs.

Rigid, soft and composite lenses have been used or envisioned for corneal reshaping or corneal refractive therapy. Corneal refractive therapy appears to have value in changing the optics of the cornea with a concomitant benefit in regulating the development of the refractive error of the eye. Recent research points to the role of light or illumination in the regulation of the development of refractive errors of the eye.

Smith and co-workers reported results of exposure of the eyes of primates to peripheral illumination as an opposite to form deprivation and found that eyes having peripheral retinal illumination exposure experienced less axial length growth than those having a lower level of illumination. (E. L. Smith III, L. Hung and J. Huang, Protective Effects of high ambient lighting on the development of form-deprivation myopia in rhesus monkeys, Iovs, December 2011, http://www.iovs.org/content/53/1/421.abstract). Further, they found these effects to be regional indicating the possible specificity of peripheral illumination.

Pugh and co-workers are developing technology for the incorporation of electronics in contact lenses. (See U.S. Patent Publication Nos. 2010/0110372, 2010/0109175, 2010/0103369, 2010/0079724, 2010/0078838, 2010/0078837 and 2010/0076553). The primary focus of these electronics is for directing information content to the central retina and for sensing ocular information including correlates to blood sugar levels and intra-ocular pressure. A number of other applications can be anticipated including the measure of inflammatory mediators in the tear film and intra-ocular blood pressure, and equivalent oxygen percentage requirements of the cornea. Pugh and co-workers have anticipated the potential to manufacture lenses with microcontrollers and energy sources.

Tieppo and co-workers have developed nano-particle technology for the purpose of sustained drug delivery to the eye. (A. Tieppo, C. J. White, A. C. Paine, M. L. Voyles, M. K. McBride, M. E. Byrne, Sustained in vivo release from imprinted therapeutic contact lenses, Journal of Controlled Release, October 2011). It is anticipated that the measure of intra-ocular pressure will be coupled with the drug delivery. In the same manner, the measure of blood sugar by way of a contact lens is anticipated to be used to regulate implanted insulin pumps. Further, the measurement of inflammatory mediators can be used to regulate the administration of anti-inflammatory agents in a lens, orally or by way of implanted pumps. The use of contact lens measuring systems coupled to pharmaceutical delivery provides value in regulating a wide range of systemic and ocular conditions.

The increase in incidence and resultant prevalence of myopia in the developed world and most particularly in Asia presents a problem of epidemic proportion. The changes in life-style, living conditions and activity preferences often prevent the ability to engage in outdoor activities. Educational, vocational and avocational demands and habits generate a set of circumstances which replace the available time for exposure to ambient outdoor light. Further, the needs to conserve energy indoors may have an ongoing effect in reducing the ambient light levels inside homes and buildings.

Research supports that the mechanism for the development of refractive error is multivariate. As such, preventive therapeutic strategies are anticipated which incorporate multiple therapeutic components.

At least two ocular components are known to change as part of refractive error development. The first is the crystalline lens geometry and the second is the vitreous chamber depth of the eye. In the normal process these anatomic components change in concert with each other to render the optical system of the eye appropriate for the vitreous chamber depth of the eye. It is also known by those skilled in the art that the equatorial diameter of the eye may vary relative to the axial length of the eye. Eyes which manifest myopia are often found to be more prolate in geometry and having an equatorial diameter which is smaller relative to their axial length than eyes manifesting hyperopia.

Researchers have identified the presence of a lower blood serum level of Vitamin D in individuals who develop myopia. (D. O. Mutti, Vitamin D receptor (VDR) and group-specific component (Vitamin D binding protein) polymorphisms in myopia, The Association for Research in vision and Ophthalmology, February 2011). A local release of neutraceuticals using time release nano-technology in a contact lens may have value when coupled with eye-wear borne illumination.

Chia et al. advanced the application of the use of muscarinic antagonists with their discovery of the efficacy of 0.01% atropine as contrasted with higher dosages having adverse side effects in children. (A. Chia, W. Chua, Y. Cheung, W. Wong, A. Lingham, A. Fong and D. Tan, Atropine for the treatment of childhood myopia, American Academy of Ophthalmology, 2011). The chronic need for the pharmaceutical suggests the value of time release in a contact lens and may have value when coupled with eye-wear borne illumination.

The role of peripheral defocus and peripheral illumination are believed to have an influence on the local growth factors which influence the shape of the crystalline lens, the equatorial diameter and the axial length of the eye.

Neitz et al. have developed a method and apparatus for limiting the growth of eye length. (See U.S. Patent Publication No. 2011/0313058). Although Neitz teaches the importance of wavelength modulation, the intervention is limited to filters that filter red light. (See, e.g., claim 17). Such filters fail to modulate brightness above an ambient level.

The work of Wildsoet in 2002 provided early evidence to the importance of light (including the wavelength of the light) for limiting the growth of eye length. (See C. Wildsoet, Recent insights from animal myopia research, BejingSeminar, November 2002).

SUMMARY OF THE INVENTION

Embodiments of the present invention provide devices and methods for eye-wear borne electromagnetic radiation refractive therapy. Eye-wear borne electromagnetic radiation refractive therapy for refractive error development regulation can be achieved by way of the incorporation of peripheral electromagnetic radiation sources which can be configured in a directional manner and can vary in the area, spectral properties and the amplitude of the radiation. Various embodiments provide direct electromagnetic radiation to the retina in a controlled manner without the reliance on the ambient light. Depending on the embodiment, this may be achieved with or without the concomitant provision of vision correction or corneal refractive therapy and with or without the use of spectral filters, and with or without the use of contact lenses.

Various embodiments of the present invention set forth spectacle frame and spectacle and contact lenses having electromagnetic radiation modulating components for the purpose of regulating the change in the ocular components which result in the presence or absence of refractive error. While the prior art (Neitz) teaches filtering red light, embodiments of the invention teach radiating with the blue end and near-visible short wavelength ultraviolet light.

According to an embodiment of the present invention, an eye-wear borne electromagnetic radiation refractive therapy system comprises: an electromagnetic radiation source comprising a ring of LEDs that directs one of its on axis or off axis electromagnetic radiation to a desired retina area of a wearer's eye; a power source for powering the LEDs, an antenna for receiving signals and a processor for controlling the LEDs; wherein the electromagnetic radiation source includes spectral characteristics present in outdoor light.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Embodiments of the invention provides an electromagnetic radiation system configured on or within a contact lens, or remote from a lens, which includes at least one electromagnetic radiation source that is directed toward the retina or passes through the eye off of the visual axis. The electromagnetic radiation sources may be light emitting diodes (LEDs), organic light emitting diodes, light reflecting from volumetric holographic reflectors or transflective films or light directed by way of birefringence, fiber optics, deflection, or reflection. The electromagnetic radiation system is configured to vary at least one of: (i) the amplitude of the radiation, (ii) the wavelength or spectral properties of the radiation, (iii) the direction of the radiation, and (iv) the area of the ocular components of the eye which are exposed to the radiation.

Figure 1:
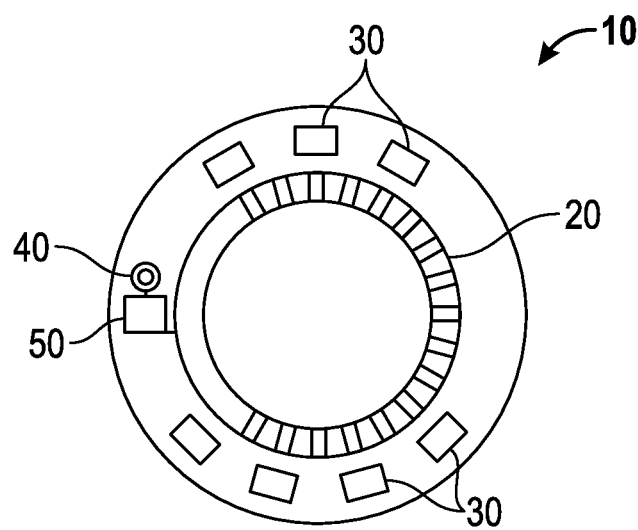
FIG. 1 illustrates a contact lens with an electromagnetic radiation source comprising a ring of LEDs that directs one of its on axis or off axis electromagnetic radiation to a desired retina area of a wearer, in accordance with an embodiment of the invention.

Referring to FIG. 1, one embodiment of the invention comprises a contact lens 10 including an "on" axis and an "off" axis. In particular, the contact lens 10 includes an electromagnetic radiation source 20 comprising a ring of LEDs that directs one of its on axis or off axis electromagnetic radiation to a desired crystalline lens area and/or a retina area of a wearer. The contacts lens 10 further comprises power source 30 for powering the LEDs, an antenna 40 for receiving signals and a controller/processor 50 for controlling the LEDs. By way of example, the LEDs may comprise Semprius LEDs. The contact lens 10 is understood to be a lens which is in contact with ocular tissue and may comprise a corneal contact lens, a scleral contact lens, a hybrid or composite contact lens, an intra-corneal lens or an intra-ocular lens.

With further reference to FIG. 1, the electromagnetic radiation source 20 is designed to have spectral characteristics present in outdoor light. One such electromagnetic radiation source 20 could be omni-directional and placed in the contact lens 10, as depicted. The electromagnetic radiation source 20 can be circular, as shown, or can be any other geometric form. In addition, the source 20 may be varied in its position or width. In this configuration, the electromagnetic radiation is expected to have undesired effects on the contrast ratio of an image falling on the central retina. An additional disadvantage is the cosmetic effect of the appearance of the forward electromagnetic radiation from the contact lens 10. A further embodiment is configured to limit the electromagnetic radiation source 20 to a direction toward the wearer's eye.

Figure 2:
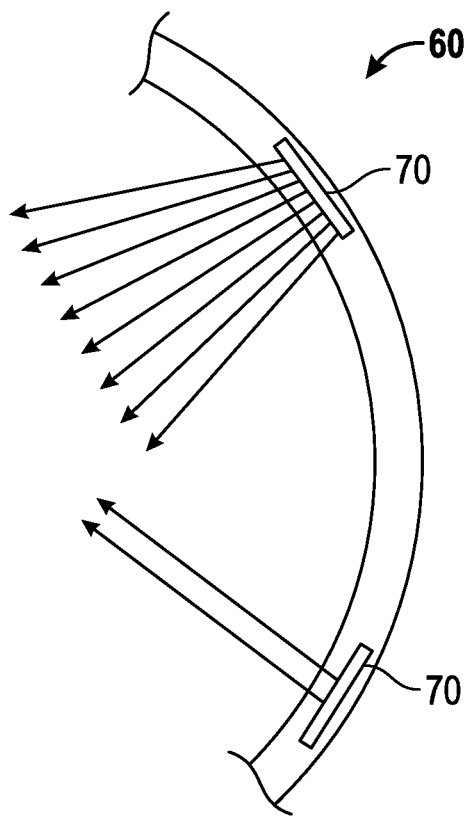
FIG. 2 illustrates a contact lens having at least one electromagnetic radiation source that is directed through the crystalline lens to a pre-determined retinal area of a wearer, in accordance with an embodiment of the invention.

FIG. 2 illustrates a contact lens 60 having at least one electromagnetic radiation source 70 that is directed through the crystalline lens to a pre-determined crystalline lens area and/or a retinal area of a wearer. The electromagnetic radiation source 70 is programmable with respect to direction, illumination, crystalline lens area and/or retinal area, amplitude, wavelength, and/or spectral property. Alternatively, the electromagnetic radiation source 70 may include a predetermined direction, illumination, crystalline lens area and/or retinal area, amplitude, and/or wavelength/spectral character.

Figure 3:
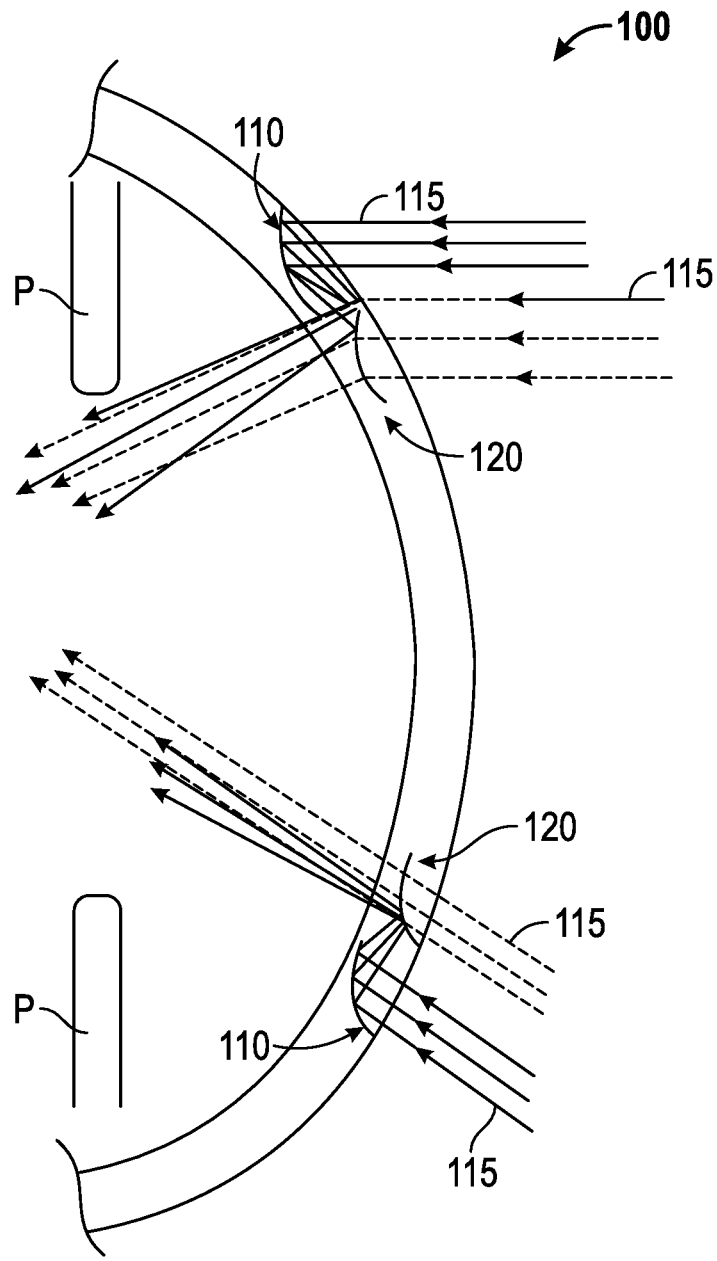
FIG. 3 illustrates a contact lens including reflective optics or folded reflective optics in the lens for the purpose of gathering light and directing the light to increase the illumination level passing through the crystalline lens and falling on a predetermined area of the retina, in accordance with an embodiment of the invention.

FIG. 3 illustrates a contact lens 100 including reflective optics or folded reflective optics in the lens for the purpose of gathering light and directing the light to increase the illumination level passing through the crystalline lens and falling on a predetermined area of the crystalline lens and/or the retina. Specifically, the optics include at least one reflective collector 110 that collects ambient light 115 and directs it toward a transreflective diffuser 120, which transmits ambient light 115 and reflects forward light from the reflective collector 110. On axis peripheral light is also collected and directed through a human pupil P.

Figure 4:
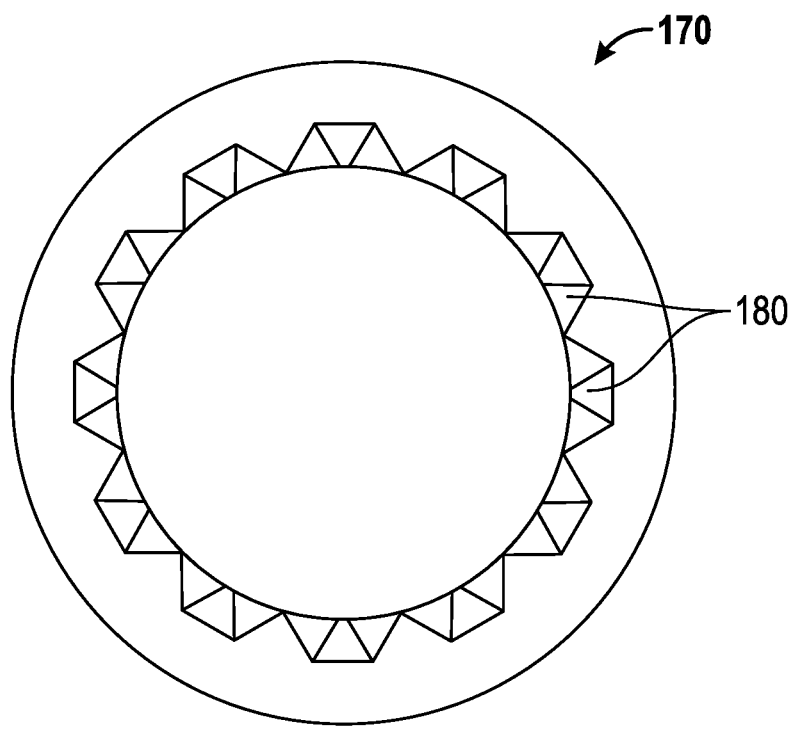
FIG. 4 illustrates a contact lens having a prismatic light collection in the contact lens, in accordance with an embodiment of the invention.

FIG. 4 illustrates a contact lens 170 having a prismatic light collection 180 in the contact lens. In the illustrated embodiment, the prismatic light collection 180 comprises a ring of deck prisms. Other configurations are possible without departing from the scope of the invention.

Figure 5:
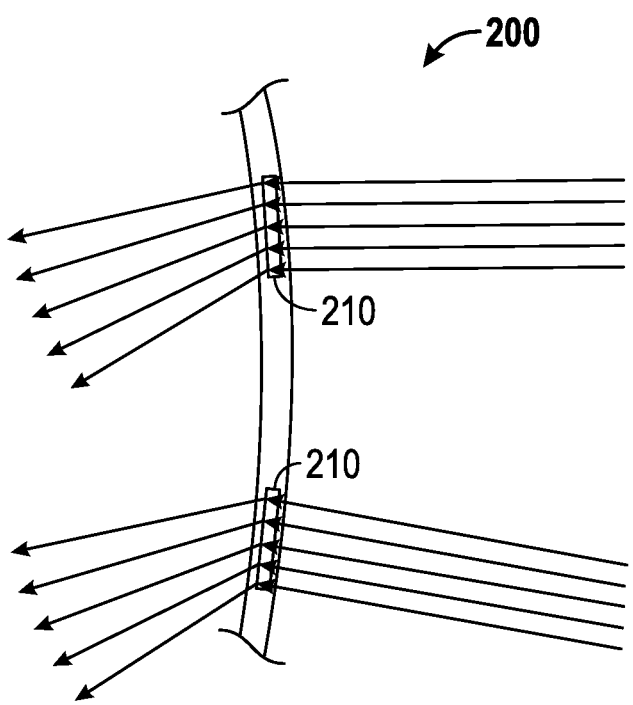
FIG. 5 illustrates a spectacle lens having deflective optics in the lens to direct a portion of the on axis or off axis light to a desired peripheral retinal level, in accordance with an embodiment of the invention.

FIG. 5 illustrates a spectacle lens 200 having deflective optics 210 in the lens 200 to direct a portion of the on axis or off axis light to a desired peripheral retinal level.

Figure 6:
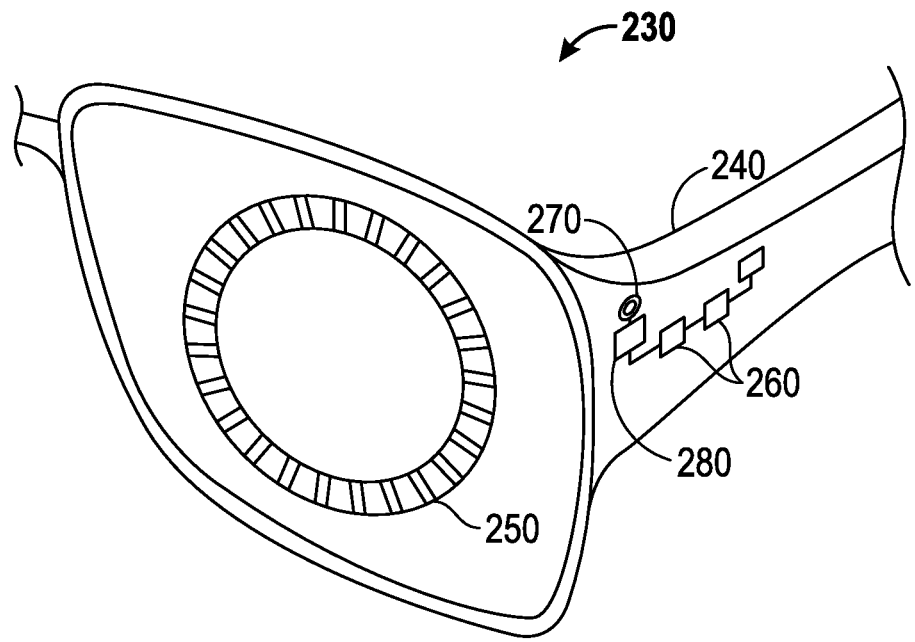
FIG. 6 illustrates a spectacle lens within a frame, wherein the spectacle lens features an electromagnetic radiation source comprising a ring of LEDs that directs one of its on axis or off axis electromagnetic radiation to a desired retina area of a wearer, in accordance with an embodiment of the invention.

FIG. 6 illustrates a spectacle lens 230 within a frame 240, wherein the spectacle lens 230 features radiation sources. Specifically, the spectacle lens 230 includes an electromagnetic radiation source 250 comprising a ring of LEDs that directs one of its on axis or off axis light to a desired retina area of the wearer's eye. The frame 240 comprises power source 260 for powering the LEDs 250, an antenna 270 and a controller/processor 280. The electromagnetic radiation source 250 is designed to have spectral properties present in solar radiation. One such electromagnetic radiation source 250 could be omni-directional and placed in the spectacle lens 230, as depicted. The electromagnetic radiation source 250 can be circular, as shown, or can be any other geometric form. In addition, the source 250 may be varied in its position or width. In this configuration, the electromagnetic radiation is expected to have undesired effects on the contrast ratio of an image falling on the central retina. An additional disadvantage is the cosmetic effect of the appearance of the forward electromagnetic radiation from the spectacle lens 230. A further embodiment is configured to limit the electromagnetic radiation source 250 to a direction toward the wearer's eye.

Figure 7:
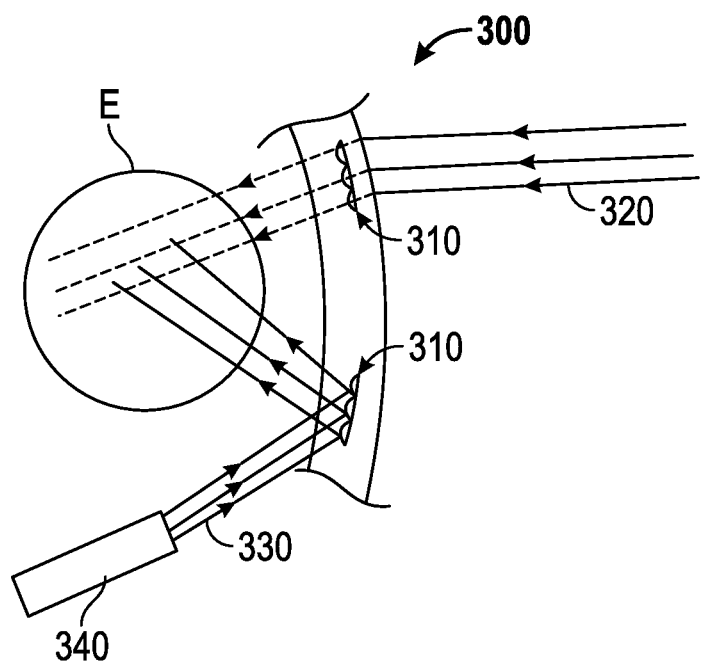
FIG. 7 illustrates a spectacle lens having at least one transreflective element that transmits ambient light to a wearer's eye and reflects projected electromagnetic radiation from an off axis projection source toward wearer's eye, in accordance with an embodiment of the invention.

FIG. 7 illustrates a spectacle lens 300 having at least one transreflective element 310 that transmits ambient light 320 to a wearer's eye E and reflects projected electromagnetic radiation from an off axis projection source 340 toward wearer's eye E.

Figure 8:
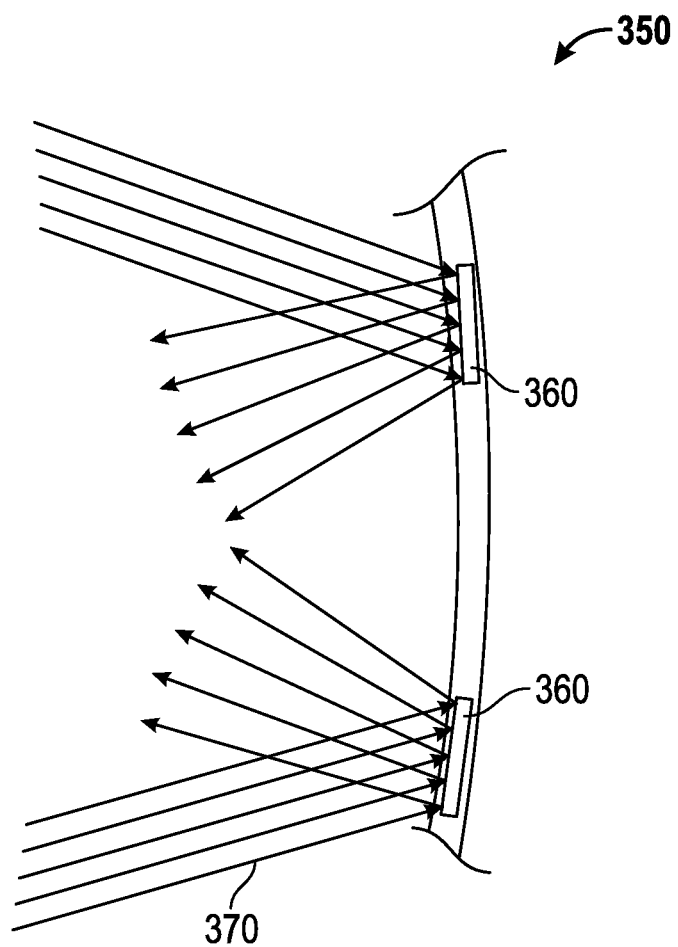
FIG. 8 illustrates a spectacle lens including at least one holographic reflector in the spectacle lens, in accordance with an embodiment of the invention.

FIG. 8 illustrates a spectacle lens 350 including at least one holographic reflector 360 in the spectacle lens 350. During use, an electromagnetic radiation source directed projected radiation 370 onto the holographic reflector 360, which reflects the radiation into the wearer's eye. By way of example, the projected radiation 370 may be provided using an LCOS projector or laser for directing the projected light 370 to a volumetric holographic reflector 360 in the spectacle lens 350, which directs the radiation in a similar manner. Similar to previous embodiments, one or more of the wavelength or spectral properties, direction, area and illumination level may be varied. In this embodiment, the transparent region directing the increased radiation allows a higher radiation level without occluding any of the peripheral field of the wearer's view.

Figure 9:
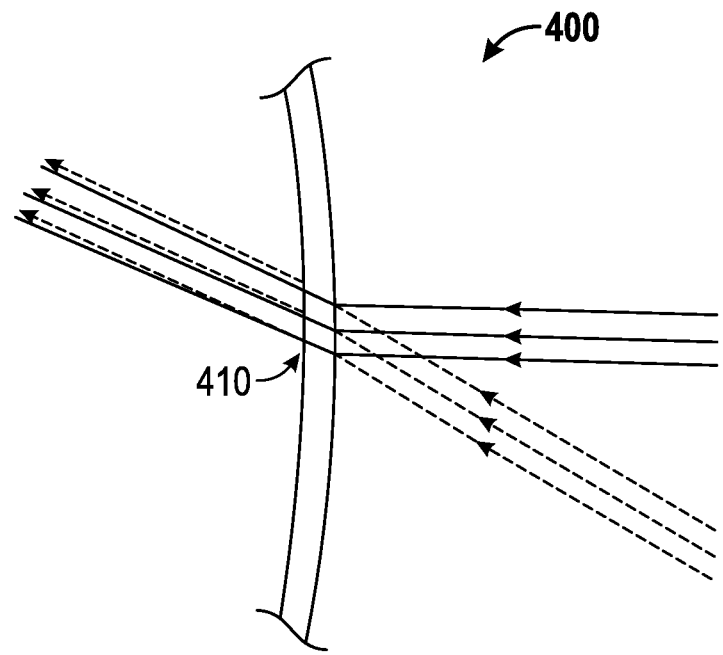
FIG. 9 illustrates a spectacle lens comprising birefringent spectacle lens optics, for the purpose of gathering light and directing the light to increase the illumination level passing through the crystalline lens and falling on a predetermined area of the retina in accordance with an embodiment of the invention.

FIG. 9 illustrates a spectacle lens 400 comprising birefringent spectacle lens optics 410, for the purpose of gathering light and directing the light to increase the illumination level passing through the crystalline lens and falling on a predetermined area of the crystalline lens and/or retina. This birefringence allows for a high on axis electromagnetic radiation source which provides the central retinal visual content to be directed off axis to increase the peripheral light level.

Figure 10:
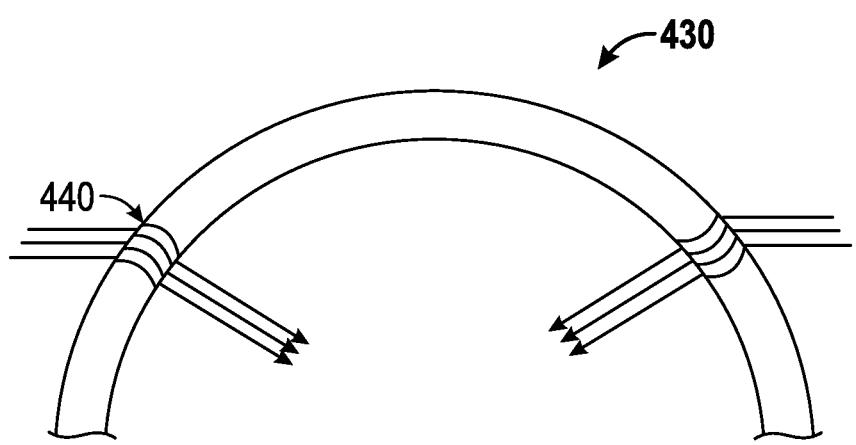
FIG. 10 illustrates a contact lens comprising fiber optics for the purpose of gathering light and directing the light to increase the illumination level passing through the crystalline lens and falling on a predetermined area of the retina, in accordance with an embodiment of the invention.

FIG. 10 illustrates a contact lens 430 comprising fiber optics 440 for the purpose of gathering light and directing the light to increase the illumination level passing through the crystalline lens and falling on a predetermined area of the retina, in accordance with an embodiment of the invention.

The electromagnetic radiation systems disclosed herein may be configured to be stable and static. In some embodiments, the electromagnetic radiation system may be configured to be programmable and dynamic. An electromagnetic radiation system may be configured as the sole therapeutic or prosthetic element in an eye-wear frame, spectacle or contact lens, or the lens system may be comprised of conventional optical corrections or therapeutic elements. For example, the spectacle or contact lens may have a refractive correction. The spectacle or contact lens-borne electromagnetic radiation system for refractive therapy may also include components for off-axis defocus optics or higher order aberration correction or therapeutic structures.

In some embodiments of the invention, an eye-wear borne illumination refractive therapy system may be configured in contact lenses used for corneal refractive therapy to reshape the cornea. One embodiment features a proximity control technology contact lens for overnight corneal reshaping comprising a lens with programmable electromagnetic radiation sources to provide a desired level of crystalline lens and/or retinal exposure during sleep for the purpose of regulating the growth of the crystalline lens or a region of the choroid and sclera underlying the retina.

In some embodiments of the invention, an eye-wear borne electromagnetic refractive therapy system may be configured is spectacle or contact lenses comprising filters intended to modulate the electromagnetic spectrum. One embodiment features a spectacle or contact lens comprising absorptive or reflective red-blocking notch filters. One skilled in the art will appreciate that the present invention intending to provide additive electromagnetic radiation can be practiced in conjunction with other filters or rugate coatings for the purpose of modulating the ambient electromagnetic radiation in a subtractive manner.

Spectacle frames, spectacle and contact lenses of this invention having electromagnetic radiation sources can be configured to have a central zone with conventional correction and electromagnetic radiation sources that are more than 10 degrees off the central axis. An electromagnetic radiation source can be more or less than 10 degrees off axis if it is deflected or reflected such that the radiation passes through the eye or is directed to a portion of the crystalline lens and/or the retina, which is approximately 10 degrees or more from the central retina. The electromagnetic radiation sources in the contact lens are configured to be between 1 and 500 microns in their widest dimension, preferably between 5 and 200 microns and most preferably between 10 and 50 microns. The electromagnetic radiation sources are configured to form an annulus to allow circumferential exposure to the retina.

In one embodiment, the electromagnetic radiation sources are individually programmed to provide a different exposure level to different sectors of the retina for the purpose of modulating the local growth factors. The electromagnetic radiation sources are selected for their spectral properties and are configured to provide a pre-determined direction and area of radiation through the crystalline lens and on the retina.

In another embodiment, the spectacle or contact lenses are configured with a sensor to measure retinal illumination. These data may be incorporated into a computer program product which in turn regulates the amplitude, direction, area or wavelength of the electromagnetic radiation sources in the system.

In yet another embodiment, the eye-wear borne electromagnetic radiation refractive therapy system may be configured in a contact lens having time release of nutraceutical or pharmaceutical agents. By example, a nutraceutical agent may be Vitamin D. By example, a pharmaceutical agent may be a muscarinic antagonist such as atropine.

Thus, it is seen that devices and methods for eye-wear borne electromagnetic radiation refractive therapy are provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative embodiments may be implemented to achieve the desired features of the present invention. Also, a multitude of different constituent part names other than those depicted herein may be applied to the various parts of the devices. Additionally, with regard to operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent.

The invention claimed is:

1. An eye-wear borne electromagnetic radiation refractive therapy system, comprising:
   at least one electromagnetic radiation source that directs its electromagnetic radiation to a desired crystalline lens or retina area of a wearer's eye;
   wherein the at least one electromagnetic radiation source is configured to vary at least one of: (i) the amplitude of the radiation, (ii) the wavelength or spectral properties of the radiation, (iii) the direction of the radiation, and (iv) the area of the ocular components of the eye which are exposed to the radiation.

2. The system of claim 1, wherein the at least one electromagnetic radiation source includes at least one spectral property present in solar radiation.

3. The system of claim 1, wherein the at least one electromagnetic radiation source includes spectral characteristics present in outdoor light.

4. The system of claim 1, wherein the eye-wear borne electromagnetic radiation refractive therapy system comprises a contact lens.

5. The system of claim 4, wherein the at least one electromagnetic radiation source is directed through the crystalline lens to a pre-determined retina area of a wearer.

6. The system of claim 5, wherein the at least one electromagnetic radiation source is programmable with respect to direction, illumination, crystalline lens area, retinal area, amplitude, wavelength, or spectral property.

7. The system of claim 1, wherein the eye-wear borne electromagnetic radiation refractive therapy system comprises a spectacle lens.

8. The system of claim 7, wherein the at least one electromagnetic radiation source is directed through the crystalline lens to a pre-determined retina area of a wearer.

9. The system of claim 1, wherein the eye-wear borne electromagnetic radiation refractive therapy system comprises a spectacle frame with at least one electromagnetic radiation source.

10. The system of claim 9, wherein the at least one electromagnetic radiation source is directed through the crystalline lens to a pre-determined retina area of a wearer.

11. An eye-wear borne electromagnetic radiation refractive therapy system, comprising:

a contact lens or spectacle lens comprising at least one optical element for redirecting electromagnetic radiation; and means for optically directing ambient light in the contact lens or spectacle lens.

12. The system of claim 11, wherein the contact lens or spectacle lens comprises reflective optics or folded reflective optics in the lens for gathering light and directing the light to modulate the electromagnetic radiation properties at a predetermined area of the crystalline lens or a predetermined area of the wearer's retina.

13. The system of claim 12, wherein the optics include at least one reflective collector that collects ambient light and directs it toward a transreflective diffuser.

14. The system of claim 13, wherein the transreflective diffuser transmits ambient light and reflects forward light from the reflective collector.

15. The system of claim 14, wherein on axis peripheral light is also collected and directed through the wearer's pupil.

16. The system of claim 11, wherein the means for optically directing ambient light comprises a prismatic light collection in the contact lens or spectacle lens.

17. The system of claim 16, wherein the prismatic light collection comprises a ring of deck prisms.

18. The system of claim 11, wherein the means for optically directing ambient light comprises birefringence.

19. The system of claim 11, wherein the means for optically directing ambient light comprises fiber optics.

* * * * *